United States Patent
Liang

(10) Patent No.: US 9,146,227 B2
(45) Date of Patent: Sep. 29, 2015

(54) PLANAR PATCH CLAMP DEVICES AND METHODS FOR FABRICATION AND USE

(75) Inventor: Yiching Liang, Milpitas, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 957 days.

(21) Appl. No.: 13/327,374

(22) Filed: Dec. 15, 2011

(65) Prior Publication Data

US 2012/0169320 A1 Jul. 5, 2012

Related U.S. Application Data

(60) Provisional application No. 61/428,414, filed on Dec. 30, 2010.

(51) Int. Cl.
*G01N 33/487* (2006.01)

(52) U.S. Cl.
CPC ... *G01N 33/48728* (2013.01); *Y10T 428/24331* (2015.01)

(58) Field of Classification Search
CPC .................. G01N 33/48728; Y10T 428/24331
See application file for complete search history.

(56) References Cited

U.S. PATENT DOCUMENTS

| 7,387,715 | B2 | 6/2008 | Vogel et al. |
| 7,723,029 | B2 | 5/2010 | Huang et al. |
| 7,968,305 | B2 | 6/2011 | Wang et al. |
| 2008/0286750 | A1 | 11/2008 | Xu et al. |

OTHER PUBLICATIONS

Behrends and Fertig, Chapter 14: "Planar Patch Clamping", Neuromethods, vol. 38: Patch-Clamp Analysis: Advanced Techniques, Second Ed., Humana Press, Inc. (2007).

*Primary Examiner* — J. Christopher Ball
*Assistant Examiner* — Maris R Kessel
(74) *Attorney, Agent, or Firm* — Bella Fishman

(57) ABSTRACT

A planar patch clamp device includes a substrate comprising a first planar surface, a second planar surface opposing the first planar surface, and an inside surface defining an aperture extending from the first planar surface to the second planar surface; and an adhesion layer conformally disposed on the substrate including on the inside surface, wherein the adhesion layer defines a shape of the aperture, and the aperture is smooth and free of sharp corners. The substrate may be composed of silicon or a silicon-inclusive compound, and the adhesion layer may be composed of a glass material having a low-temperature reflow property. The device may be annealed to reflow the adhesion layer, thereby providing the aperture with smooth surfaces.

24 Claims, 9 Drawing Sheets

| Ch | mmHg | Re (MΩ) | Ce (pF) | Rseal (MΩ) | Cm (pF) | Rm (MΩ) | Ra (MΩ) | Ra range (MΩ) | Sweep | Trial | Step | State (Expt 773, Cell 333) |
|---|---|---|---|---|---|---|---|---|---|---|---|---|
| 1 | 0 | 0.9 | 0.0 | sealed 1178 | 14.5 | 1012 | 12.4 | 8.7 - 13.2 | 3055... | 1 | 6/18 | Wait 60 s (45 s remaining) |
| 2 | 0 | 1.3 | 0.0 | sealed 958 | 7.2 | 5984 | <5.6 | 5.5 - 6.0 | 1865... | 1 | 5/18 | Washout 86 s (43 s remaining) |
| 3 | 0 | 0.9 | 0.0 | sealed 1064 | 10.1 | 5245 | <2.5 | 2.4 - 2.5 | 2355... | 1 | 5/18 | Washout 86 s (7 s remaining) |
| 4 | 0 | 0.9 | 0.0 | sealed 1112 | 4.9 | 1047 | <6.2 | 7.3 - 8.2 | 8555... | 1 | 4/18 | Wait 60 s (28 s remaining) |
| 5 | 0 | 0.9 | 0.0 | sealed 1069 | 7.3 | 4607 | <5.5 | 5.1 - 5.5 | 2355... | 1 | 5/18 | Washout 86 s (16 s remaining) |
| 6 | 0 | 0.8 | 0.0 | sealed 985 | 8.9 | 1896 | <4.0 | 3.8 - 4.1 | 2265... | 1 | 5/18 | Washout 86 s (23 s remaining) |
| 7 | 0 | 1.0 | 0.0 | sealed 1041 | 10.6 | 5390 | <3.8 | 3.7 - 4.0 | 2255... | 1 | 5/18 | Washout 86 s (24 s remaining) |
| 8 | 0 | 0.9 | 0.0 | sealed 1814 | 13.1 | 17615 | <3.1 | 3.0 - 3.2 | 2355... | 1 | 5/18 | Washout 86 s (22 s remaining) |
| 9 | 0 | 0.9 | 0.0 | sealed 1022 | 8.8 | 2828 | <4.1 | 4.0 - 4.3 | 1955... | 1 | 5/18 | Washout 86 s (40 s remaining) |
| 10 | 0 | 0.8 | 0.0 | sealed 1216 | 8.6 | 288 | <4.6 | 4.4 - 4.7 | 1955... | 1 | 5/18 | Washout 86 s (37 s remaining) |
| 11 | 0 | 0.8 | 0.0 | sealed 1011 | 10.4 | 2138 | <3.8 | 3.7 - 4.0 | 1955... | 1 | 5/18 | Washout 86 s (40 s remaining) |
| 12 | 0 | 0.9 | 0.0 | sealed 1934 | 9.6 | 2876 | <4.2 | 3.9 - 4.2 | 1955... | 1 | 5/18 | Washout 86 s (38 s remaining) |
| 13 | 0 | 0.9 | 0.0 | sealed 3528 | 7.3 | 309 | <5.4 | 4.9 - 5.6 | 1755... | 1 | 5/18 | Washout 86 s (46 s remaining) |
| 14 | 0 | 0.8 | 0.0 | sealed 2365 | 10.3 | 113 | <2.8 | 2.7 - 2.9 | 2055... | 1 | 5/18 | Washout 86 s (34 s remaining) |
| 15 | 0 | 1.2 | 0.0 | sealed 969 | 8.1 | 2407 | <4.4 | 4.3 - 4.6 | 1165... | 1 | 4/18 | Wait 60 s (11 s remaining) |
| 16 | 0 | 1.0 | 3.2 | sealed 890 | 14.2 | 565 | <2.8 | 2.7 - 2.9 | 1455... | 1 | 5/18 | Washout 86 s (62 s remaining) |

Seal resistance at each channel

Fig. 7B

PLANAR PATCH CLAMP DEVICES AND METHODS FOR FABRICATION AND USE

RELATED APPLICATIONS

This application claims the benefit of U.S. Provisional Patent Application Ser. No. 61/428,414, filed Dec. 30, 2010, titled "PLANAR PATCH-CLAMP DEVICE FOR ELECTROPHYSIOLOGY", the content of which is incorporated by reference herein in its entirety.

TECHNICAL FIELD

The present invention generally relates generally to patch clamp electrophysiology, and particularly to planar patch clamp devices utilized to form giga-ohm seals with live biological cells.

BACKGROUND

Patch clamp techniques are utilized in electrophysiology to enable the study of single or multiple ion channels in biological cells and other tissues. In a traditional patch clamp technique, a cell is provided in a bath solution, and a glass micropipette having an inside diameter of about 1 μm is pressed against the surface of the membrane of a cell. The portion of the membrane surface of the cell covered by the micropipette is known as the "patch." A small amount of suction is applied through the micropipette to form a high-resistance seal between the cell membrane and the micropipette. The micropipette is filled with an electrolyte, a silver chloride electrode (wire) is inserted into the electrolyte and a grounded electrode may be placed in contact with the bath, thereby enabling the measurement of electrical current resulting from ion flow through the ion channel associated with the patch. The high resistance of the seal formed between the cell membrane and the micropipette functions to electrically isolate the current being measured and minimize the signal-to-noise ratio of the measurement being recorded. It is typically desired that the resistance of the seal be as high as 1 GΩ or higher; such seals are termed "giga-ohm seals" or "gigaseals."

Patch clamps employing micropipettes increasingly are being replaced by planar patch clamp devices. Planar patch clamp devices are generally provided in the form of microfabricated substrates. Planar patch clamp devices include planar substrates with apertures of 1-2 μm in diameter that function as the tips of micropipettes. Suction and/or an electric field are applied so as to position a cell on the aperture, and the high-resistance seal is formed between the cell membrane and the substrate in the vicinity of the aperture. The substrate may serve as a partition between respective fluid compartments located above and below the substrate, with the aperture fluidly interconnecting the two fluid compartments. A measurement electrode may be placed in the fluid compartment in which the cell resides, and a grounded electrode may be placed in the other fluid compartment.

Planar patch clamp devices are amenable to high-throughput assaying systems and cooperation with microfluidic components. The substrates have typically been composed of quartz or glass. Some commercially available glass substrates have proprietary coatings designed to enhance the ability to form giga-ohm seals (i.e., increase the success rate in forming giga-ohm seals). Alternative substrate materials have also been proposed, such as silicon as disclosed in U.S. Pat. No. 7,387,715. This patent describes a number of planar structures for positioning cells and performing electrical and/or optical analyses related to the presence and activity of ion channels, but does not teach any particular combination of low-cost materials and configurations that would be optimal for the formation of high-quality giga-ohm seals.

High seal resistance between the living cell and the substrate of a planar patch clamp device is highly desirable for achieving high-quality recordings of ion channel activities. Therefore, there is an ongoing need for providing planar patch clamp devices capable of achieving high seal resistance at a reasonable cost. There is also a need for providing planar patch clamp devices capable of reliably forming high-quality giga-ohm seals with high success rates.

SUMMARY

To address the foregoing problems, in whole or in part, and/or other problems that may have been observed by persons skilled in the art, the present disclosure provides methods, processes, systems, apparatus, instruments, and/or devices, as described by way of example in embodiments set forth below.

According to one implementation, a planar patch clamp device includes a substrate comprising a first planar surface, a second planar surface opposing the first planar surface, and an inside surface defining an aperture extending from the first planar surface to the second planar surface; and an adhesion layer conformally disposed on the substrate including on the inside surface, wherein the adhesion layer defines a shape of the aperture, and the aperture is smooth and free of sharp corners.

According to another implementation, the planar patch clamp device includes a membrane layer disposed on the substrate such that the membrane layer covers the first planar surface and the second planar surface while exposing the aperture at the first planar surface and at the second planar surface, wherein the adhesion layer is conformally disposed on the membrane layer such that the membrane layer is between the first planar surface and the adhesion layer and between the second planar surface and the adhesion layer.

According to another implementation, the aperture extending from the first planar surface to the second planar surface is a first aperture, the membrane layer comprises a suspended membrane spanning the first aperture at the second planar surface, the suspended membrane comprises an inside edge defining a second aperture communicating with the first aperture, the adhesion layer is conformally disposed on the inside edge and defines a shape of the second aperture, and the second aperture is smooth and free of sharp corners.

According to another implementation, a planar patch clamp device includes a substrate comprising a first planar surface, a second planar surface opposing the first planar surface, and an inside surface defining a cavity, wherein a cavity opening is located at the first planar surface; a membrane layer disposed on the substrate such that the membrane layer covers the first planar surface while exposing the cavity opening, and the membrane layer covers the second planar surface to define a suspended membrane spanning the cavity, wherein the suspended membrane includes an aperture communicating with the cavity; and an adhesion layer conformally disposed on the inside surface and the membrane layer, wherein the adhesion layer includes an inside edge defining the aperture, and the inside edge is smooth and free of sharp corners.

In some implementations, the substrate has a thickness of 200 μm or greater. In other implementations, the substrate has a thickness of less than 200 μm.

In some implementations, the planar patch clamp device includes a plurality of apertures.

According to another implementation, a method for monitoring ion flow across a membrane of a biological cell includes introducing a fluid in the first fluid chamber and the second fluid chamber of the planar patch clamp device; positioning the biological cell on the aperture; forming an electrically resistant seal between the membrane and the adhesion layer at the aperture; and reading an electrical signal transmitted by the electrode.

According to another implementation, a method for fabricating a planar patch clamp device includes forming an inside surface through a substrate such that the inside surface extends from a first planar surface to an opposing second planar surface of the substrate, wherein the inside surface defines an aperture, and the substrate is composed of silicon or a silicon-inclusive compound; depositing an adhesion layer composed of a glass material conformally on the substrate including on the inside surface, wherein the adhesion layer defines a shape of the aperture; and annealing the planar patch clamp device to reflow the adhesion layer, wherein the aperture is smooth and free of sharp corners.

According to another implementation, before depositing the adhesion layer, the method includes depositing a membrane layer conformally on the substrate, wherein depositing the adhesion layer comprises depositing the adhesion layer conformally on the membrane layer, such that the membrane layer is between the first planar surface and the adhesion layer and between the second planar surface and the adhesion layer.

According to another implementation, the method includes: at a first etching site, etching through the membrane layer to the first planar surface to expose a portion of the first planar surface; and at a second etching site opposite the first etching site, etching through the membrane layer to the second planar surface to expose a portion of the second planar surface. Forming the inside surface includes contacting the exposed portion of the first planar surface or the second planar surface with an etchant to etch through the substrate.

According to another implementation, the aperture defined by the inside surface is a first aperture, and the method includes: at a first etching site, etching through the membrane layer to the first planar surface to expose a portion of the first planar surface; and at a second etching site opposite to the first etching site, etching through the membrane layer to the second planar surface to form a second aperture. Forming the inside surface includes contacting the exposed portion of the first planar surface with an etchant to etch through the substrate, such that the first aperture communicates with the second aperture, the membrane layer comprises a suspended membrane that spans the first aperture, and the second aperture is formed through the suspended membrane. Depositing the adhesion layer includes depositing the adhesion layer conformally on the suspended membrane such that the adhesion layer defines a shape of the second aperture, and after annealing the second aperture is smooth and free of sharp corners.

According to another implementation, a method for fabricating a planar patch clamp device includes depositing a membrane layer conformally on a substrate, wherein the substrate comprises a first planar surface and a second planar surface opposing the first planar surface; defining a first etching site on the first planar surface and a second etching site on the second planar surface; at the second etching site, etching through the membrane layer to the second planar surface to form an aperture through the membrane layer; at the first etching site, etching through the membrane layer to the first planar surface to form an opening through which a portion of the first planar surface is exposed; at the exposed portion, etching through the substrate to form a cavity that communicates with the aperture, wherein the membrane layer comprises a suspended membrane that spans the cavity and the aperture is formed through the suspended membrane; depositing an adhesion layer conformally on the membrane layer and an inside surface of the substrate defining the cavity, wherein an inside edge of the adhesion layer defines the aperture; and annealing the planar patch clamp device to reflow the adhesion layer, wherein the inside edge is smooth and free of sharp corners.

According to another implementation, a planar patch clamp device fabricated according to methods disclosed herein is provided.

In various implementations, the substrate may be composed of silicon or a silicon-inclusive compound, the membrane layer may be composed of silicon nitride, and the adhesion layer may be composed of a glass material having a low-temperature reflow property, such as phosphosilicate glass, borosilicate glass, or borophosphosilicate glass.

In some implementations, the adhesion layer has a surface roughness ranging from 1 to 20 nm. In some implementations, the adhesion layer has a surface roughness ranging from 5 to 10 nm.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIGS. 7A and 7B illustrate a sixteen-channel recording of measured current (in nA) over time (in msec) for sixteen patch clamps made between respective apertures of the planar patch clamp device and live cells, and associated data including measured seal resistance (in MΩ).

DETAILED DESCRIPTION

Figure 1:
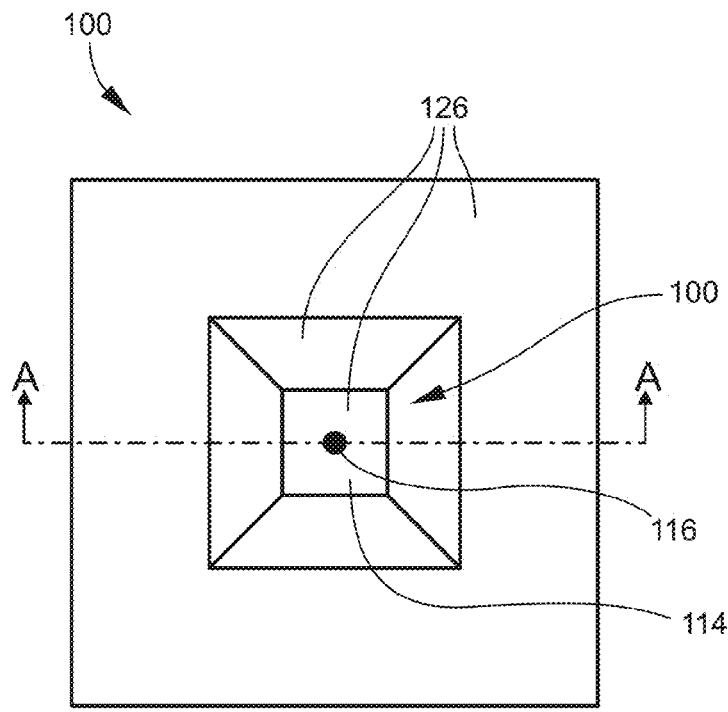
FIG. 1 is a planar view of an example of a planar patch clamp device according to one implementation.
Figure 2:
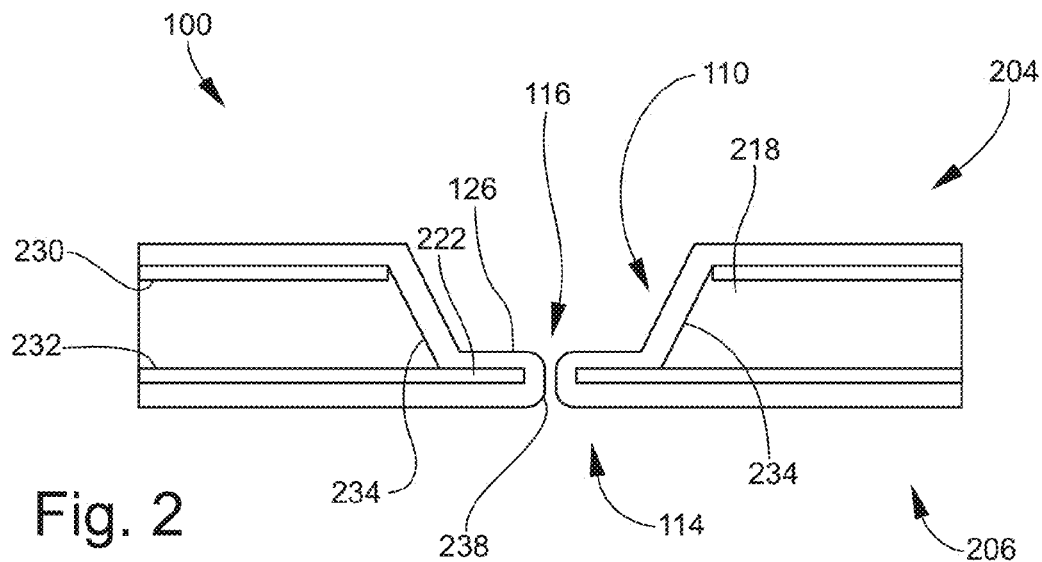
FIG. 2 is a cross-sectional side view of the planar patch clamp device taken along line A-A in FIG. 1.

FIG. 1 is a planar view and FIG. 2 is a cross-sectional side view of an example of a planar patch clamp device 100 according to one implementation. The planar patch clamp device 100 generally includes a body that has a first side 204, an opposing second side 206, and a thickness in a direction generally perpendicular to the first side 204 and the second side 206. A cavity 110 in the body opens at the first side 204 and terminates at a suspended membrane 114 at the second side 206. The suspended membrane 114 has an aperture 116 formed through its thickness. The aperture 116 is in open communication with the cavity 110. The membrane 114 is "suspended" in that it spans the open cross-sectional area defined by the cavity 110 at the second side 206. Elsewhere in the present disclosure, the cavity 110 may be referred to as a first aperture and the aperture 116 may be referred to as a second aperture.

The body includes a substrate 218, a membrane layer 222 disposed on the substrate 218, and an adhesion layer 126 disposed on the membrane layer 222. The substrate 218 generally includes a first planar surface 230, an opposing second planar surface 232, and one or more inside walls or surfaces 234 extending through the thickness of the substrate 218 that define the cavity 110. The membrane layer 222 coats the first planar surface 230 and second planar surface 232 of the substrate 218, but may not coat the inner wall(s) 234 defining the cavity 110. The adhesion layer 126 may conformally coat all exposed areas of the substrate 218 and the membrane layer 222, including the inner wall(s) 234 of the substrate 218 and the portion (inside edge) of the suspended membrane 114 surrounding the aperture 116. Hence, an inside edge 238 of the adhesion layer 126 ultimately defines the shape (i.e., profile, geometry, etc.) and size (e.g., diameter) of the aperture 116. The diameter of the aperture 116 should be sized so as to be effective for patching live cells. In some implementations, the diameter of the aperture 116 ranges from about 1 to 5 μm. In some implementations, it has been found particularly effective for the diameter of the aperture 116 to be about 2 μm. From the cross-sectional perspective of FIG. 2, the substrate 218 may be considered as being interposed between a first portion of the membrane layer 222 on the first side 204 and a second portion of the membrane layer 222 on the second side 206. Additionally, on the first side 204 the first portion of the membrane layer 222 may be considered as being interposed between the substrate 218 and a first portion of the adhesion layer 126, and on the second side 206 the second portion of the membrane layer 222 may be considered as being interposed between the substrate 218 and a second portion of the adhesion layer 126. Moreover, the adhesion layer 126 ultimately defines the shape and size (e.g., tapering cross-sectional area) of the cavity 110 as well as the aperture 116.

The substrate 218 should be rigid, i.e., thick enough to provide mechanical integrity and robustness for the planar patch clamp device 100 to enable the planar patch clamp device 100 to reliably withstand handling during fabrication, subsequent packaging, and subsequent use (which may entail, for example, loading into an automated assaying system). Generally, the thickness of the substrate 218 varies depending on its composition and whether it is provided by a commercial supplier in a predetermined range of thicknesses. In some implementations, the thickness of the substrate 218 is about 200 μm or greater. In some implementations, the thickness of the substrate 218 ranges from about 200 μm to about 1 mm. The substrate 218 should be composed of a material that is sufficiently rigid at the foregoing thicknesses, compatible with the microfabrication process described below, readily available, and relatively low cost. In some implementations the substrate 218 is composed of silicon, which is readily available and easily processed by well-established manufacturing techniques developed by the integrated circuit (IC) industry, and thus is a low-cost material. In one example, the substrate 218 is a commercially available silicon substrate having a thickness of 450 μm. In other implementations, however, the thickness of the substrate 218 may be less than 200 μm. Alternatively, the substrate 218 may be composed of a silicon-inclusive compound (e.g., oxide, nitride, oxynitride, carbide, etc.).

The membrane layer 222 may be any material that is compatible for deposition on the substrate 218, provides an excellent surface for depositing the adhesion layer 126, and is suitable for serving as a mask during the fabrication process described below. In some implementations, the membrane layer 222 is composed of silicon nitride ($S_3N_4$). Silicon nitride has been found, for example, to present a low-stress surface on which to successfully deposit phosphosilicate glass uniformly and without cracking. As used herein, the term "silicon nitride" includes silicon nitride compounds with or without any added dopants such as, for example, oxygen. The thickness of the membrane layer 222 should be small enough to provide a short pathway for fluid to pass through the aperture 116, yet large enough to withstand etching (described below) and agitation in a wet bath. The thickness of the membrane layer 222 may generally range from less than 1 μm to tens of μm. In some implementations, the thickness of the membrane layer 222 ranges from about 1 μm to about 10 μm. In other implementations, the thickness of the membrane layer 222 ranges from about 1 μm to about 5 μm. In one specific yet non-limiting implementation, the thickness of the membrane layer 222 is about 1 μm. In some implementations, the size (planar area) of the suspended membrane 114 may range, for example, between about 50 to 100 μm$^2$ but in other implementations may be larger than 100 μm$^2$. In still other implementations, the suspended membrane 114 may be as small as the aperture 116, i.e., just large enough to define the aperture 116.

The adhesion layer 126 may be any material capable of being conformally deposited and "reflowed" as described below, and which provides a smooth surface capable of excellent binding to cells and consequently forming a giga-ohm seal. The adhesion layer 126 may be composed of any material with good low-temperature reflow properties. As an example, a material having a low-temperature reflow property is one that, after deposition on a surface, will reflow when subjected to annealing at a temperature ranging from, for example, about 500° C. to about 1000° C. Examples of materials having a low-temperature reflow property include, but are not limited to, certain glass materials. Examples of such glass materials include, but are not limited to, silicate-based glasses with or without boron and/or phosphorous species, such as phosphosilicate glass (PSG), i.e., a silicate glass ($SiO_2$) doped with a low level (e.g., 4%) of phosphorous; borosilicate glass (BSG); and borophosphosilicate glass (BPSG). The thickness of the adhesion layer 126 determines the overall capacitance of the planar patch clamp device 100, which is limited by the specific instrument employed for making the data recordings. A greater thickness results in lower capacitance, which is more desirable, but greater thicknesses may be more difficult and costly to produce. Moreover, the thickness of the adhesion layer 126 determines the final diameter of the aperture 116. In some implementations, the thickness of the adhesion layer 126 ranges from about 1 to 20 μm, which provides a reasonable compromise between ease and cost of manufacture and good performance. In other implementations, the thickness of the adhesion layer 126 may be greater than 20 μm. Referring to FIG. 2, in one example in which the thickness of the membrane layer 222 is about 1 μm and the thickness of the adhesion layer 126 is about 5 to 6 μm, the total thickness of the resulting suspended membrane 114 (the membrane layer 222 covered on both sides with the adhesion layer 126) ranges from about 10 μm to about 12 μm.

In some implementations, the planar patch clamp device 100 includes a single aperture 116 and associated cavity 110. In other implementations, the planar patch clamp device 100 may include a plurality of apertures 116 and associated cavities 110. In such implementations, the apertures 116 (and associated cavities 110) may be arranged as a linear series (i.e., a single row or column) of apertures 116 or as a two-dimensional array of apertures 116.

An example of a method for fabricating the planar patch clamp device 100 will now be described in accordance with one implementation. First, a substrate 218 as described above is provided and placed in a suitable reaction chamber. The surfaces of the substrate 218 may be cleaned, treated, planarized, polished, heated or otherwise prepared as needed for deposition of the membrane layer 222. In the reaction chamber, a membrane layer 222 as described above is then conformally deposited to a uniform thickness on all exposed surfaces of the substrate 218. In typical implementations, a suitable vacuum deposition process is employed. As one example in the case of silicon nitride, a chemical vapor deposition (CVD) technique may be employed using appropriate gas-phase silicon and nitrogen precursor compounds. The membrane layer 222 is then patterned and etched on the first side 204 and the second side 206 by employing any suitable photolithography and wet (chemical) etching and/or dry (plasma) etching techniques. Patterning may be done with standard photolithographic techniques using UV photoresist and a photomask, followed by etching. A direct material removal process such as laser ablation or mechanical drilling may also be used. The pattern on the first side 204 defines the etch site(s) for the cavity 110 (cavities), and the pattern on the second side 206 defines the etch site(s) for the aperture(s) 116. For example, on the first side 204 (at a first etching site), the membrane layer 222 may be etched through its thickness to the first planar surface 230 of the substrate 218, thereby forming an opening in the membrane layer 222 that exposes a portion of the first planar surface 230. On the second side 206 (at a second etching site, typically opposite to the first etching site in the direction of the layer thicknesses), the membrane layer 222 may be etched through its thickness to the second planar surface 232 of the substrate 218, thereby forming an opening (corresponding to the aperture 116 in the present implementation) in the membrane layer 222 that exposes a portion of the second planar surface 232. The aperture 116 is formed within the area (e.g., at the center) where the suspended membrane 114 is to be formed. Dry (plasma) etching is typically utilized when etching the membrane layer 222 although wet etching may alternatively be utilized.

The cavity 110 may then be formed by removing substrate material, i.e., the inside surface 234 is formed through the substrate 218 such that the inside surface 234 extends from the first planar surface 230 to the second planar surface 232, thereby defining the cavity 110. The cavity 110 may be formed by performing any suitable wet and/or dry etching technique through the opening of the membrane layer 222 that was formed on the first side 204, such as by contacting the exposed portion of the first planar surface 230 with a wet and/or dry etchant Wet etching may be performed using an isotropic etchant or an anisotropic etchant. The most common isotropic etchant for silicon is HNA, mixture of hydrofluoric acid (HF), nitric acid ($HNO_3$), and acetic acid ($CH_3COOH$). Common anisotropic etchants for silicon include alkali hydroxides (e.g. KOH, NaOH) and other hydroxides (e.g. TMAH, or Tetramethyl Ammonium Hydroxide). Other wet etchants may be suitable, as appreciated by persons skilled in the art. Dry etching with a plasma or reactive ion etching system may also be used when a smaller cavity 110 (cavities) is desired, but the process is more expensive. Anisotropic etching may result in the cavity 110 having a pyramidal or frusta-conical shape, as illustrated by example in FIGS. 1 and 2. After forming the cavity 110, the portion of the membrane layer 222 on the second side 206 that covers or spans the cavity 110 remains, i.e., the suspended membrane 114 is defined. The as-formed cavity 110 extends between the first planar surface 230 and the suspended membrane 114 and communicates with the aperture 116. Alternatively, the aperture 116 may be formed after forming the cavity 110.

At this stage, the structural features defining the aperture 116 include the flat inside edge of the suspended membrane 114 bounded by sharp (angled) corners at the transitions to the planar sides of the suspended membrane 114. An aperture with sharp or angled features (i.e., abrupt geometrical transitions) is characteristic of conventional planar patch clamp devices, and is a primary reason why most conventional devices have a lower than desirable success rate in forming good giga-ohm seals. The addition of the adhesion layer 126 in accordance with the present disclosure addresses this problem. The adhesion layer 126 is conformally deposited on all exposed surfaces of the substrate 218 (i.e., the inner wall 234) and the membrane layer 222, utilizing any suitable thermal oxidation or vacuum deposition technique. In particular, the adhesion layer 126 coats the inside edge of the suspended membrane 114 to define the shape and size of the aperture 116. After deposition of the adhesion layer 126, the planar patch clamp device 100 is placed in a suitable oven and annealed at a temperature sufficient to cause the material of the adhesion layer 126 to "reflow." The annealing temperature required depends on the composition of the adhesion layer 126 and may range, for example from about 500° C. to about 1000° C. As one non-limiting example, annealing may be performed at 950° C. for 30 minutes in the case of 4% PSG. Annealing at a lower temperature typically requires a longer duration.

Figure 3:
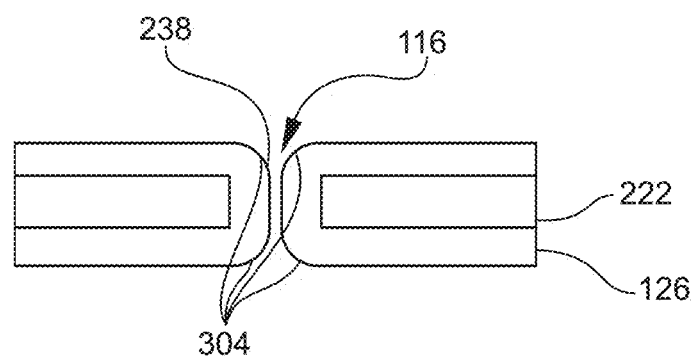
FIG. 3 is a cross-sectional side view of the region of an aperture illustrated in FIG. 2.

FIG. 3 is a cross-sectional side view of the region of the aperture 116 after reflowing the adhesion layer 126. It can be seen that the reflowing process smoothes out any sharp features of the aperture 116. As a result, the aperture 116 has smooth, rounded features, e.g., the inside edge 238 and smooth, rounded corners 304 of the adhesion layer 126 that provide the transitions from the inside edge 238 to the planar portions of the adhesion layer 126. These smooth, rounded features are optimal for forming a giga-ohm seal with a cell under study. That is, the aperture 116 is free of any sharp corners, sharp edges, and other abrupt transitions in its geometry. In some implementations, the adhesion layer 126, or at least the portion of the adhesion layer 126 surrounding (defining) the aperture 116 (e.g., the inside edge 238, rounded corners 304, and immediately surrounding planar areas) has a surface roughness ranging from about 1 nm to about 20 nm. In other implementations, the surface roughness ranges from about 5 to about 10 nm.

Figure 4A:
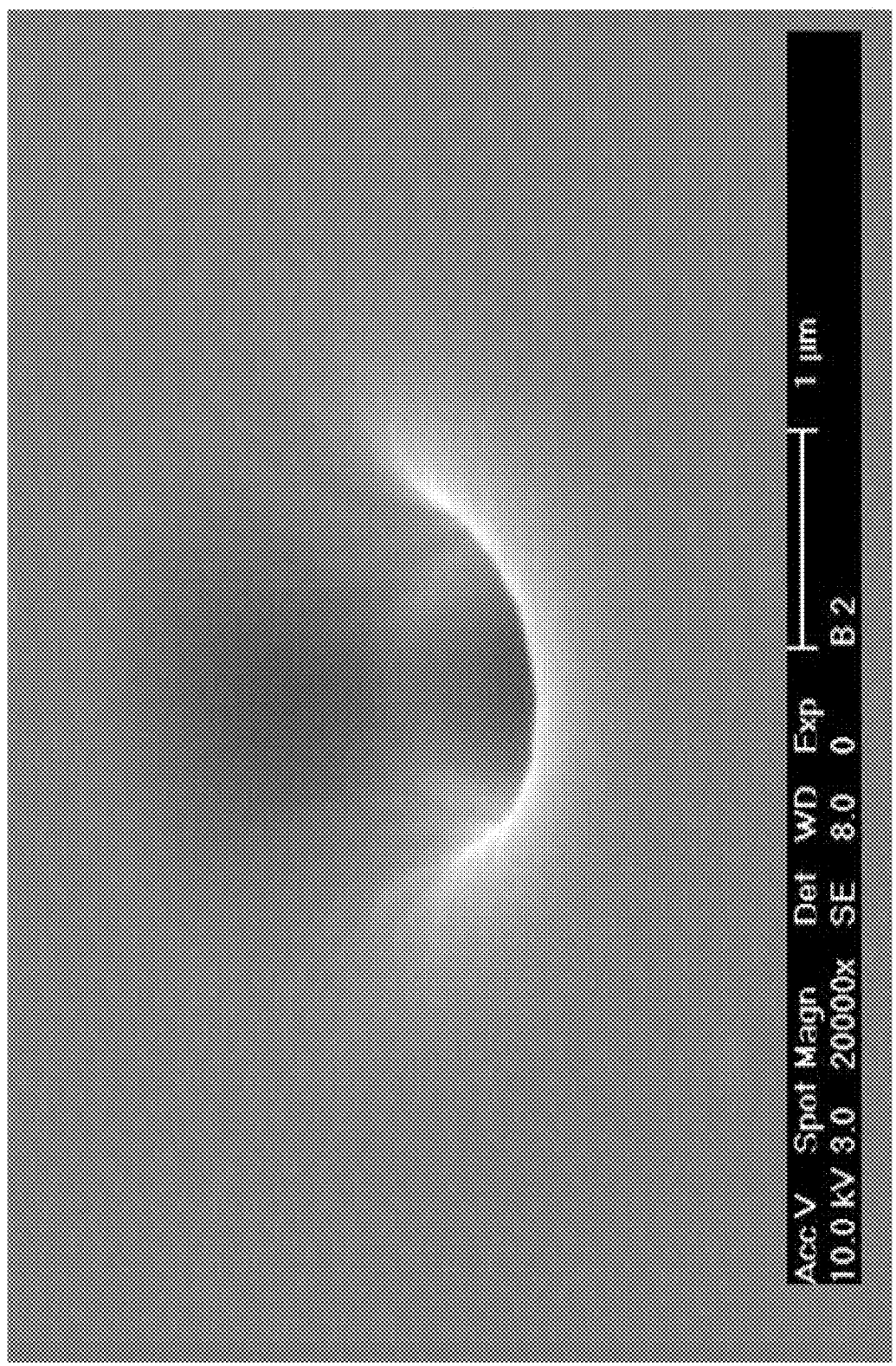
FIGS. 4A and 4B are SEM images of the aperture of an actual planar patch clamp device fabricated in accordance with the present disclosure, after completion of a reflow process.
Figure 4B:
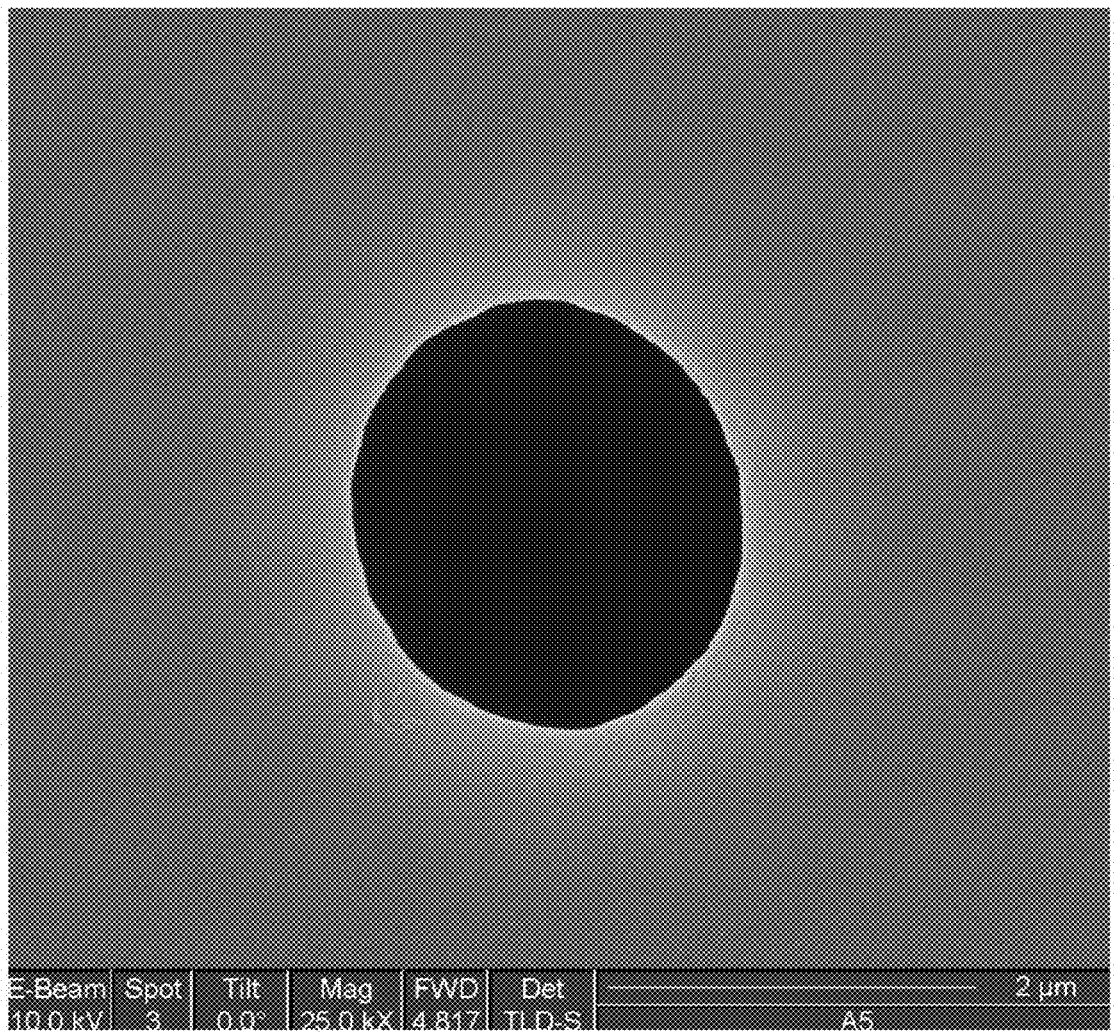
Figure 5:
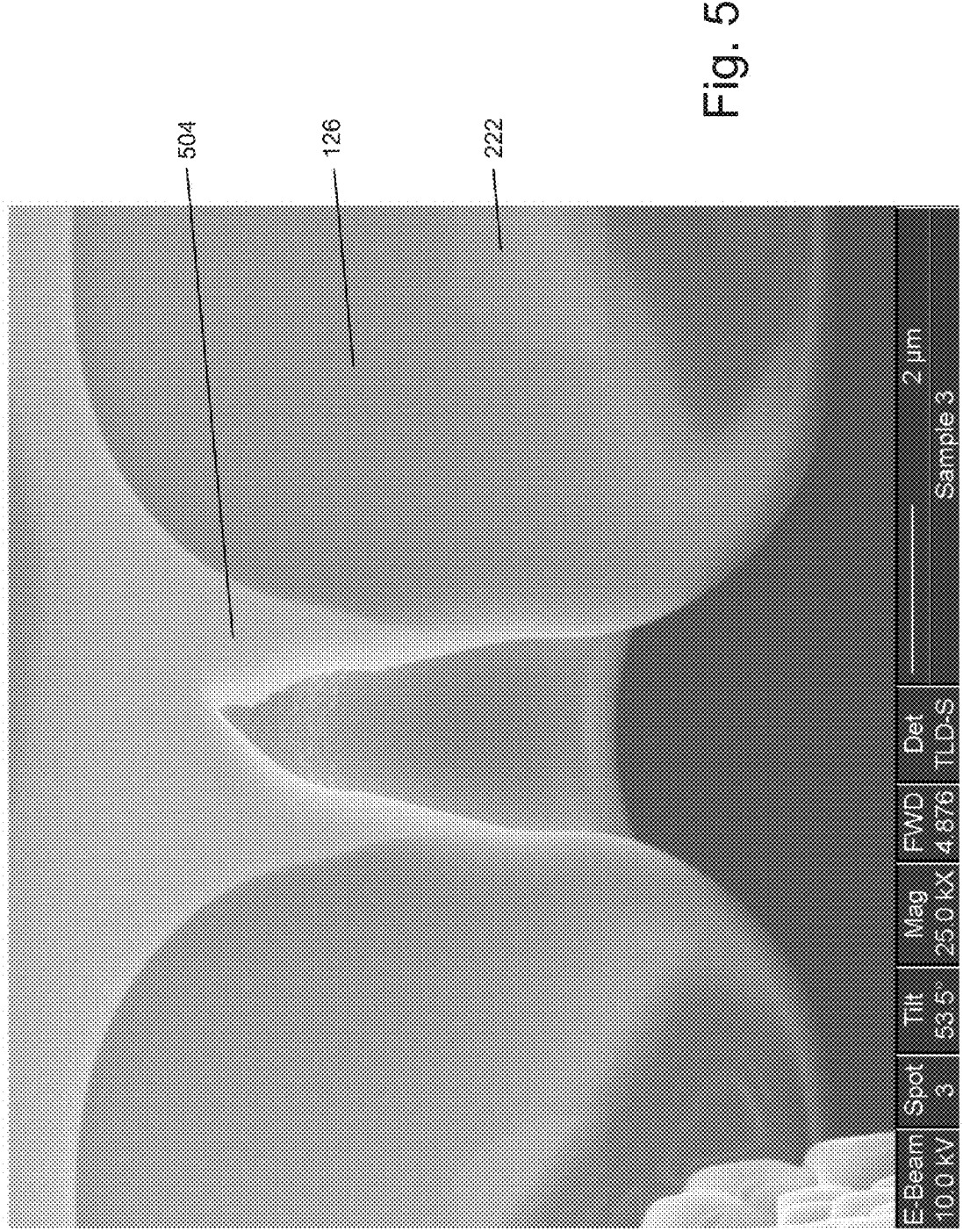
FIG. 5 is a cross-sectional SEM image of the aperture illustrated in FIGS. 4A and 4B.

FIGS. 4A and 4B are SEM images of the aperture 116 of an actual planar patch clamp device 100 after completion of the reflow process, further demonstrating the resulting smooth, rounded features. FIG. 5 is a cross-sectional SEM image of the aperture 116, further showing the smooth geometry of the aperture 116. A metal layer 504 was deposited on the upper portion of the aperture 116 for testing purposes only, i.e., to obtain the SEM image.

Figure 6:
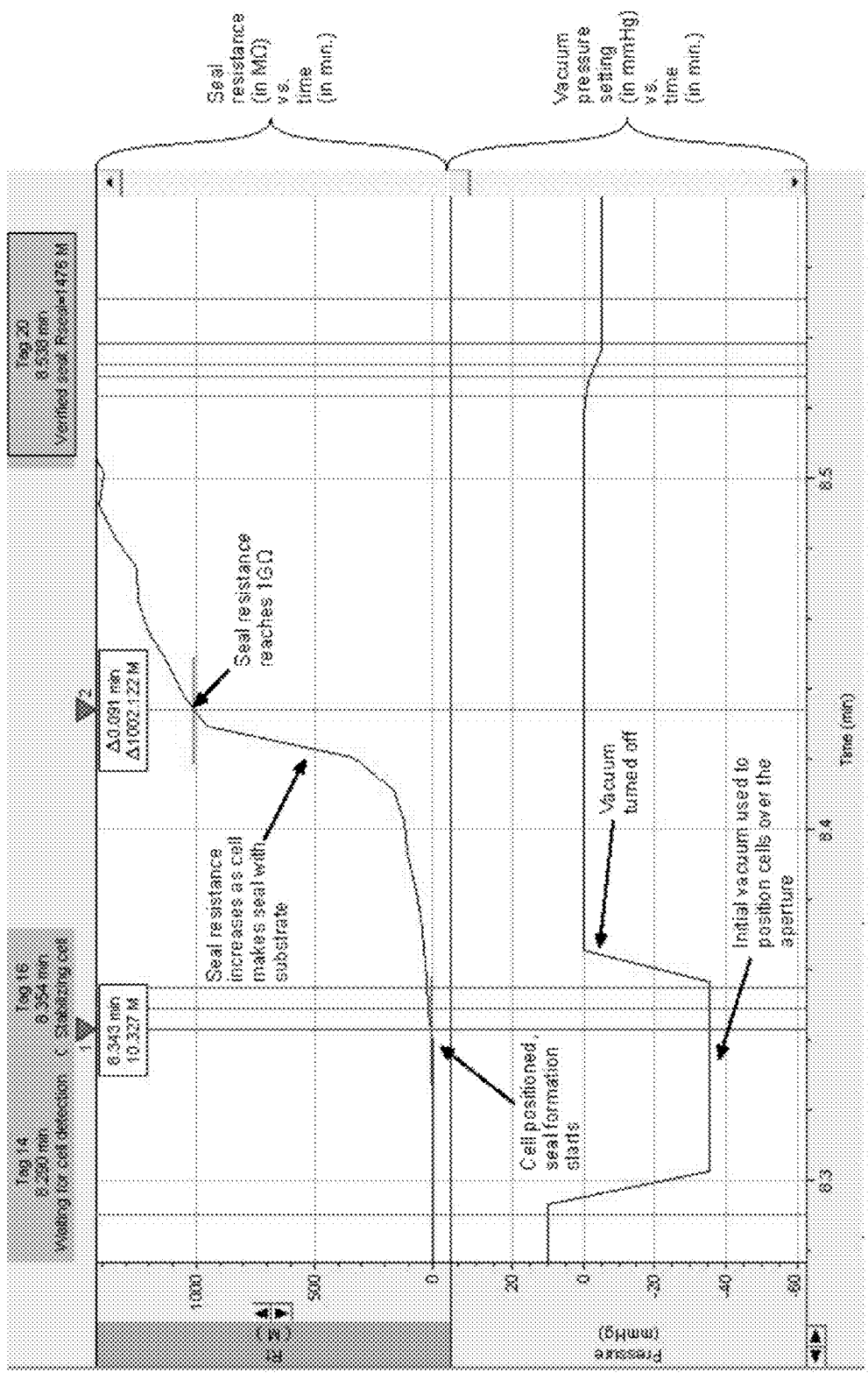
FIG. 6 illustrates a recording of seal resistance (in MΩ) between a planar patch clamp device fabricated in accordance with the present disclosure and a live cell over time (in minutes), and the vacuum pressure (in mm Hg) applied to position the cell at the aperture of the planar patch clamp device.

FIG. 6 illustrates an actual recording of seal resistance (in MΩ) between the planar patch clamp device 100 and a live cell over time (in minutes) and the vacuum pressure (in mm Hg) applied to position the cell at the aperture 116. The recording was obtained by operating the planar patch clamp device 100 in a PatchXpress® 7000A system equipped with PatchXpress® Commander Software, commercially available from Molecular Devices, LLC, Sunnyvale, Calif. FIG. 6 shows the respective points in time at which the initial vacuum is applied to position the cell over the aperture, the cell is successfully positioned and seal formation begins, the vacuum is turned off, a rapid increase in seal resistance occurs as the seal is formed, and the seal resistance reaches 1 GΩ FIG. 6 demonstrates that a giga-ohm seal is formed in less than a tenth of a minute after the initial vacuum is applied.

Figure 7A:
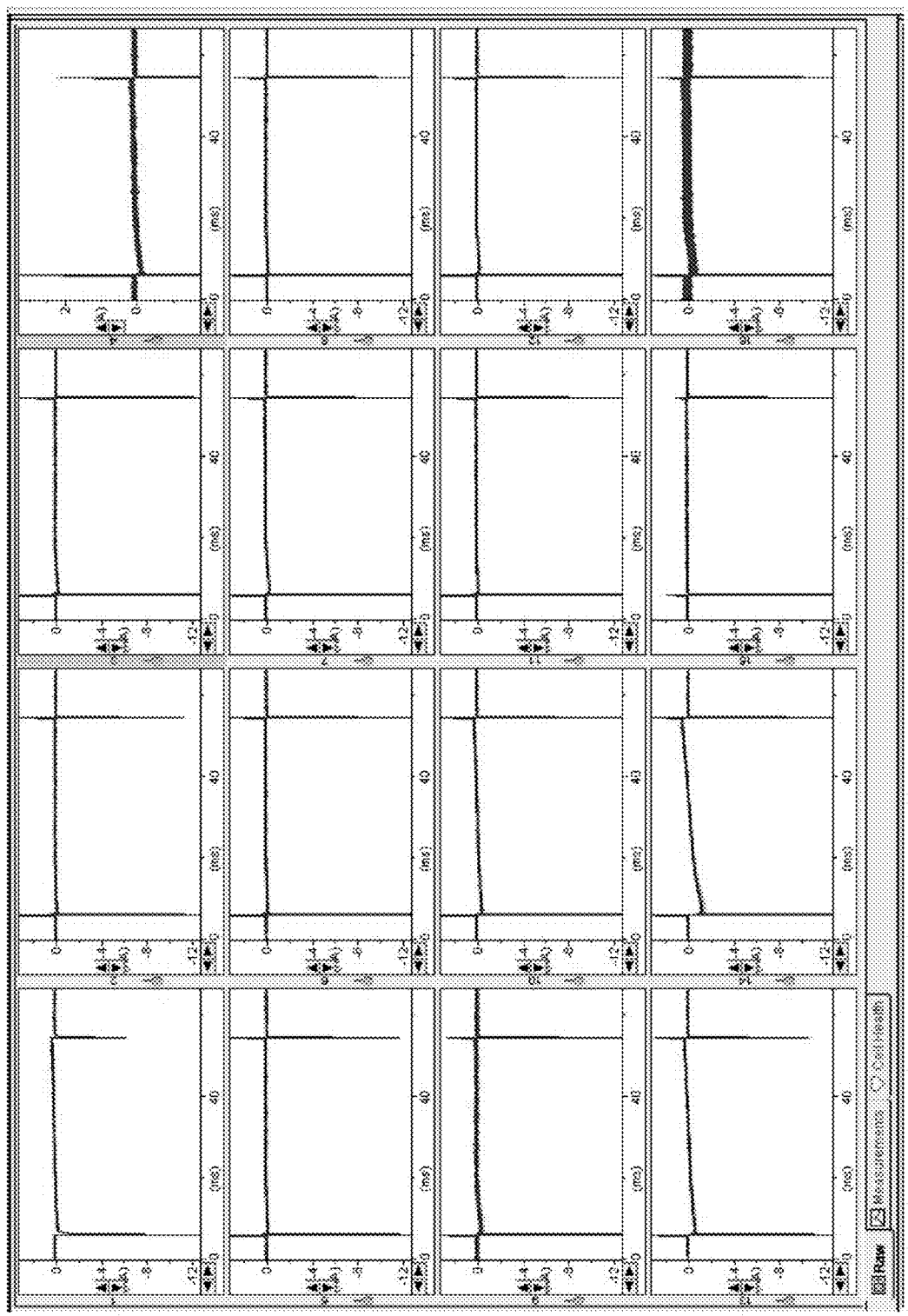

FIGS. 7A and 7B illustrates an actual sixteen-channel recording of measured current (in nA) over time (in msec) for sixteen patch clamps made between respective apertures 116 of the planar patch clamp device 100 and live cells, and associated data including measured seal resistance (in MΩ). FIGS. 7A and 7B demonstrate giga-ohm seal formation in each of the sixteen channels. The recording was obtained by operating PatchXpress® 7000A system equipped with PatchXpress® Commander Software.

The TABLE below presents experimental data comparing the performance of a planar patch claim device 100 fabricated as described above to that of a SealChip® planar patch clamp device commercially available from AVIVA Biosciences Corporation, San Diego, Calif. The experimental data are the results of multiple tests employing both devices using three different cell lines, HEK-hERG, CHO-hERG, and RBL. The results demonstrate that the device 100 disclosed herein enables a higher percentage of giga-ohm seals to be formed with all three cell lines, and with a substantial reduction in cost of manufacturing.

TABLE

| | Cell lines | | | | | |
| --- | --- | --- | --- | --- | --- | --- |
| | HEK-hERG cells | | CHO-hERG cells | | RBL cells | |
| | Sample size/Seal resistance | | | | | |
| | Sample size | % GΩ | Sample size | % GΩ | Sample size | % GΩ |
| AVIVA SealChip ® | 241 | 49% | 77 | 70% | 209 | 66% |
| Device of present disclosure | 489 | 60% | 194 | 81% | 406 | 84% |

Figure 8:
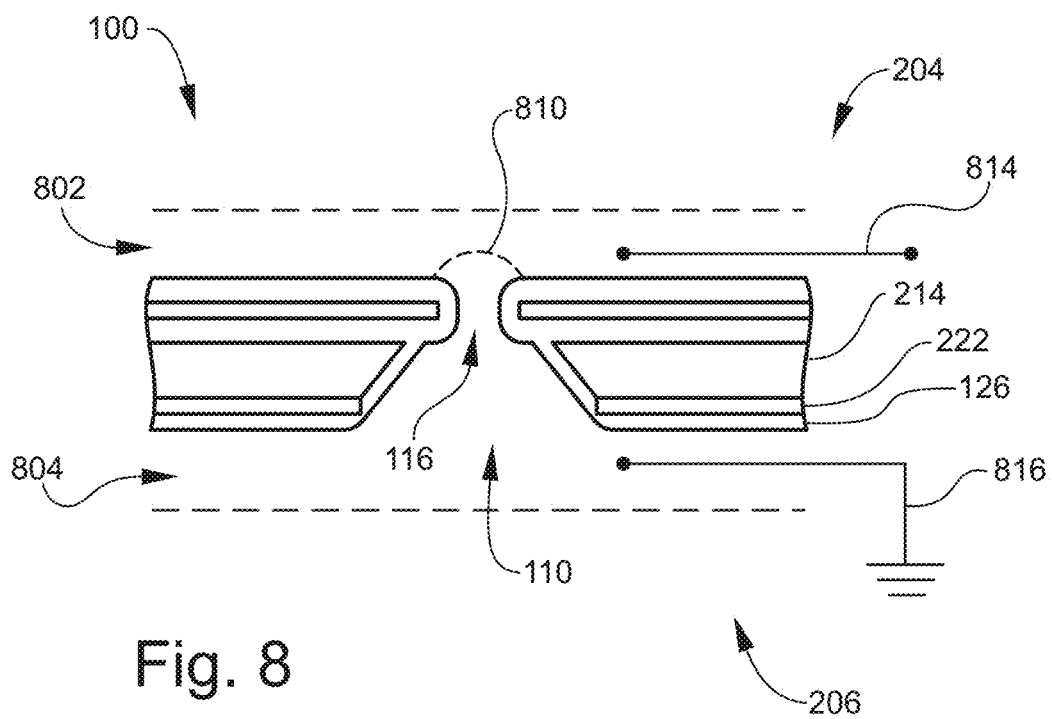
FIG. 8 is a cross-sectional side view of the planar patch clamp device illustrated in FIGS. 1 and 2, with additional components schematically illustrated.

FIG. 8 is a cross-sectional side view of the planar patch clamp device 100 with additional components schematically illustrated. A first fluid chamber 802 is provided on the first side 204 and a second fluid chamber 804 is provided on the second side 206. The fluid chambers 802 and 804 may have any structure (e.g., one or more walls, etc.) suitable for containing desired volumes of fluid on either side of the aperture 116 where a biological cell (or tissue, etc.) 810 is positioned during an experiment. That is, the fluid chambers 802 and 804 may enclose, or be attached to, the substrate/membrane layer/adhesion layer composite of the planar patch clamp device 100 by any suitable means, such that the first fluid chamber 802 encloses a first volume adjacent to the first planar surface 230 and communicating with the aperture 116, the second fluid chamber 804 encloses a second volume adjacent to the second planar surface 232 and communicating with the aperture 116, and the aperture 116 provides fluid communication (fluidly interconnects) the first fluid chamber 802 and the second fluid chamber 804. The walls or other structural components defining the fluid chambers 802 and 804 may have any suitable compositions such as those often employed in microfluidics applications (e.g., quartz, fused silica, certain polymers having an inertness adequate for patch clamp experiments, etc.). The fluid chambers 802 and 804 may be part of, or supported by, a housing of the planar patch clamp device 100 that is configured for use in an electrophysiology instrument or system, such as an automated system capable of handling multiple samples, a few examples of which are noted below. The fluid chambers 802 and 804 may include ports configured as desired for facilitating filling the fluid chambers 802 and 804 with fluid, removing fluid from the fluid chambers 802 and 804, rinsing and cleaning the fluid chambers 802 and 804, introducing and removing biological cells, etc. One or more ports may, for example, be configured for coupling with a fluid handling system (e.g., tubing, pumps, valves, etc.). The fluid utilized may be any fluid suitable for patch clamp analysis, such as, for example, an electrolyte, ionic solution, etc., as appreciated by persons skilled in the art.

As also shown in FIG. 8, the planar patch clamp device 100 may include a first electrode (or measurement electrode) 814 extending into the first fluid chamber 802, and a second electrode (or reference electrode) 816 extending into the second fluid chamber 804. In typical implementations, the electrodes 814 and 816 are silver or chlorided silver (Ag/Cl) wires. The electrodes 814 and 816 may be coupled to any suitable electronics (e.g., amplifier, voltage source, signal conditioning circuitry, computing device, display/readout device, etc.) configured for acquiring current measurements, as appreciated by persons skilled in the art. The reference electrode 816 is the electrode positioned on the opposite side of the aperture 116 as the sample cell 810, and is typically grounded. In alternative implementations, the planar patch clamp device 100 may be flipped (i.e., oriented as shown in FIG. 2) and the sample cell 810 positioned in the cavity 110. In this case, the measurement electrode 814 would be located in the fluid chamber 804 that encloses the cavity 110.

As one example of using the planar patch clamp device 100, ion flow across a membrane of a biological cell may be monitored by introducing a fluid in the first fluid chamber 802 and the second fluid chamber 804. The biological cell may be introduced into one of the fluid chambers 802 and 804 by any means, such as in suspension with the fluid introduced into one of the fluid chambers 802 and 804. The biological cell may then be positioned on the aperture 116 by any means, such as by utilizing suction and/or an electric field. An electrically resistant seal (preferably a giga-ohm seal) is then formed between the membrane and the adhesion layer 126 at the aperture 116. An electrical signal (e.g., current) resulting from activity of the ion channel(s) being monitored is transmitted by the appropriately positioned electrode 814, and is read, processed and interpreted by any suitable technique known to persons skilled in the art.

In implementations where the planar patch clamp device 100 includes a plurality of apertures 116, respective pairs of first fluid chambers 802 and second fluid chambers 804 (and corresponding first and second electrodes 814 and 816) may be provided for each aperture 116. Alternatively, the same first fluid chamber 802 and second fluid chamber 804 (and corresponding first and second electrodes 814 and 816) may be in communication with a subset of the apertures 116, or all of the apertures 116.

Figure 9:
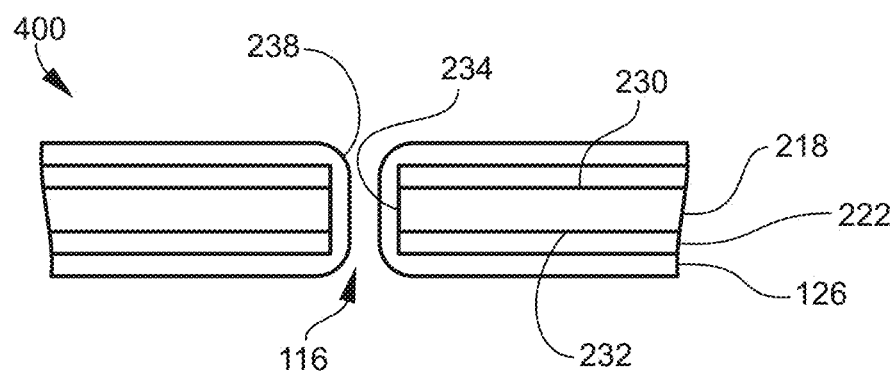
FIG. 9 is a cross-sectional side view of an example of a planar patch clamp device according to another implementation.

FIG. 9 is a cross-sectional side view of an example of a planar patch clamp device 900 according to another implementation. The planar patch clamp device 900 includes the substrate 218, membrane layer 222, adhesion layer 126, and aperture 116 as described above in conjunction with the planar patch clamp device 900 illustrated in FIGS. 1 and 2. In this implementation, the substrate 218 is thin enough that the aperture 116 may be suitably formed by etching through the substrate 218 and membrane layer 222 without the assistance of the cavity 110 described above. In some implementations, the substrate 218 is less than 200 µm. In some implementations, the substrate 218 is about 100 µm or less. In a case where a chemical etchant is utilized, the membrane layer 222 may function as an etch mask, as in the implementation described above. Moreover, the substrate 218 may be thin enough that the aperture 116 may be suitably formed by etching through the substrate 218 by a more direct method such as, for example, laser ablation. In this case, the membrane layer 222 may be eliminated and the adhesion layer 126 may be directly deposited (and subsequently reflowed during annealing) on the substrate 218.

As one example of fabricating the planar patch clamp device 900, the inside surface 234 is formed through the substrate 218 such that the inside surface 234 extends from the first planar surface 230 to the second planar surface 232, thereby defining the aperture 116. The inside surface 234 may be formed directly, such as by laser ablation or mechanical drilling, or by employing a dry or wet etchant. The adhesion layer 126 is then deposited conformally on the substrate 218, including on the inside surface 234, whereby the adhesion layer 126 defines the shape and size of the aperture 116. The planar patch clamp device 900 is then annealed as described above to reflow the adhesion layer 126, whereby the resulting aperture 116 is smooth and free of sharp corners.

As described above and illustrated in FIG. 9, before depositing the adhesion layer 126, a membrane layer 222 may be deposited conformally on the substrate 218. In this case, the adhesion layer 126 is conformally deposited on the exposed portions of the membrane layer 222 as well as on the inside surface 234. When the membrane layer 222 is to be included, patterning and etching techniques as described earlier in this disclosure may be employed. For example, at a first etching site, the membrane layer 222 may be etched through to the first planar surface 230 to expose a portion of the first planar surface 230. At a second etching site, the membrane layer 222 may be etched through to the second planar surface 232 to expose a portion of the second planar surface 232. In this case, the inside surface 234 may be formed by contacting the exposed portion of the first planar surface 230 or the second planar surface 232 with an etchant to etch through the substrate 218.

A planar patch clamp device 100 or 900 as described herein may be utilized in any patch clamp application, including attached-cell and whole-cell applications, and manual or automated high-throughput applications. As non-limiting examples, the planar patch clamp device 100 or 900 may be utilized as a consumable device in automated parallel patch clamp systems configured for directly recording ion channel activity in whole-cell path clamp screening assays, such as in the PatchXpress®, IonWorks Quattro®, and IonWorks Barracuda® systems commercially available from Molecular Devices, LLC, Sunnyvale, Calif.

For purposes of the present disclosure, it will be understood that when a layer (or coating, film, region, substrate, component, device, or the like) is referred to as being "on" or "over" another layer, that layer may be directly or actually on (or over) the other layer or, alternatively, intervening layers (e.g., buffer layers, transition layers, interlayers, sacrificial layers, etch-stop layers, masks, electrodes, interconnects, contacts, or the like) may also be present. A layer that is "directly on" another layer means that no intervening layer is present, unless otherwise indicated. It will also be understood that when a layer is referred to as being "on" (or "over") another layer, that layer may cover the entire surface of the other layer or only a portion of the other layer. It will be further understood that terms such as "formed on" or "disposed on" are not intended to introduce any limitations relating to particular methods of material transport, deposition, fabrication, surface treatment, or physical, chemical, or ionic bonding or interaction.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A planar patch clamp device, comprising:
   a substrate composed of silicon or a silicon-inclusive compound and comprising a first planar surface, a second planar surface opposing the first planar surface, and an inside surface defining an aperture extending from the first planar surface to the second planar surface; and
   an adhesion layer composed of a glass material having a low-temperature reflow property, the adhesion layer conformally disposed on the substrate including on the inside surface, wherein the adhesion layer defines a shape of the aperture, and the aperture is smooth and free of sharp corners.

2. The planar patch clamp device of claim 1, wherein the aperture has an inside diameter ranging from 1 to 5 µm.

3. The planar patch clamp device of claim 1, wherein the adhesion layer has a thickness ranging from 1 to 20 µm.

4. The planar patch clamp device of claim 1, wherein the adhesion layer has a surface roughness ranging from 1 to 20 nm.

5. The planar patch clamp device of claim 1, wherein the glass material is selected from the group consisting of phosphosilicate glass, borosilicate glass, and borophosphosilicate glass.

6. The planar patch clamp device of claim 1, comprising a membrane layer composed of silicon nitride and disposed on the substrate such that the membrane layer covers the first planar surface and the second planar surface while exposing the aperture at the first planar surface and at the second planar surface, wherein the adhesion layer is conformally disposed on the membrane layer such that the membrane layer is between the first planar surface and the adhesion layer and between the second planar surface and the adhesion layer.

7. The planar patch clamp device of claim 6, wherein the membrane layer has a thickness ranging from 1 to 10 µm.

8. The planar patch clamp device of claim 6, wherein the aperture extending from the first planar surface to the second planar surface is a first aperture, the membrane layer comprises a suspended membrane spanning the first aperture at the second planar surface, the suspended membrane comprises an inside edge defining a second aperture communicating with the first aperture, the adhesion layer is conformally disposed on the inside edge and defines a shape of the second aperture, and the second aperture is smooth and free of sharp corners.

9. The planar patch clamp device of claim 1, comprising a first fluid chamber enclosing a first volume adjacent to the first planar surface, and a second fluid chamber enclosing a second volume adjacent to the second planar surface, wherein the aperture fluidly interconnects the first fluid chamber and the second fluid chamber.

10. The planar patch clamp device of claim 9, comprising an electrode extending into at least one of the first fluid chamber and the second fluid chamber.

11. A method for monitoring ion flow across a membrane of a biological cell, the method comprising:
introducing a fluid in the first fluid chamber and the second fluid chamber of the planar patch clamp device of claim 10;
positioning the biological cell on the aperture;
forming an electrically resistant seal between the membrane and the adhesion layer at the aperture; and
reading an electrical signal transmitted by the electrode.

12. A method for fabricating a planar patch clamp device, the method comprising:
forming an inside surface through a substrate such that the inside surface extends from a first planar surface to an opposing second planar surface of the substrate, wherein the inside surface defines an aperture, and the substrate is composed of silicon or a silicon-inclusive compound;
depositing an adhesion layer composed of a glass material conformally on the substrate including on the inside surface, wherein the adhesion layer defines a shape of the aperture; and
annealing the planar patch clamp device to reflow the adhesion layer, wherein the aperture is smooth and free of sharp corners.

13. The method of claim 12, wherein the aperture has an inside diameter ranging from 1 to 5 μm.

14. The method of claim 12, wherein the adhesion layer has a thickness ranging from 1 to 20 μm.

15. The method of claim 12, wherein the adhesion layer has a surface roughness ranging from 1 to 20 nm.

16. The method of claim 12, wherein annealing is performed at a temperature ranging from 500° C. to 1000° C.

17. The method of claim 12, comprising performing laser ablation or mechanical drilling to form the inside surface.

18. The method of claim 12, comprising, before depositing the adhesion layer, depositing a membrane layer conformally on the substrate, wherein depositing the adhesion layer comprises depositing the adhesion layer conformally on the membrane layer, such that the membrane layer is between the first planar surface and the adhesion layer and between the second planar surface and the adhesion layer.

19. The method of claim 18, wherein the membrane layer has a thickness ranging from 1 to 10 μm.

20. The method of claim 18, comprising:
at a first etching site, etching through the membrane layer to the first planar surface to expose a portion of the first planar surface;
at a second etching site opposite the first etching site, etching through the membrane layer to the second planar surface to expose a portion of the second planar surface; and
wherein forming the inside surface comprises contacting the exposed portion of the first planar surface or the second planar surface with an etchant to etch through the substrate.

21. The method of claim 18, wherein the aperture defined by the inside surface is a first aperture, and further comprising:
at a first etching site, etching through the membrane layer to the first planar surface to expose a portion of the first planar surface;
at a second etching site opposite to the first etching site, etching through the membrane layer to the second planar surface to form a second aperture;
wherein forming the inside surface comprises contacting the exposed portion of the first planar surface with an etchant to etch through the substrate, such that the first aperture communicates with the second aperture, the membrane layer comprises a suspended membrane that spans the first aperture, and the second aperture is formed through the suspended membrane; and
wherein depositing the adhesion layer comprises depositing the adhesion layer conformally on the suspended membrane such that the adhesion layer defines a shape of the second aperture, and after annealing the second aperture is smooth and free of sharp corners.

22. The method of claim 21, wherein etching through the membrane layer comprises dry etching, and etching through the substrate comprises anisotropic etching.

23. A planar patch clamp device fabricated by forming an inside surface through a substrate defining an aperture such that the inside surface extends from a first planar surface to an opposing second planar surface of the substrate composed of silicon or a silicon-inclusive compound;
depositing a membrane layer conformally on the substrate;
depositing an adhesion layer composed of a glass material conformally on the substrate including on the inside surface such that the membrane layer is between the first planar surface and the adhesion layer and between the second planar surface and the adhesion layer, wherein the adhesion layer defines a shape of the aperture; and
annealing the planar patch clamp device to reflow the adhesion layer, wherein the aperture is smooth and free of sharp corners.

24. A planar patch clamp device fabricated by forming an inside surface through a substrate such that the inside surface extends from a first planar surface to an opposing second planar surface of the substrate, wherein the inside surface defines an aperture, and the substrate is composed of silicon or a silicon-inclusive compound;
depositing an adhesion layer composed of a glass material conformally on the substrate including on the inside surface, wherein the adhesion layer defines a shape of the aperture; and
annealing the planar patch clamp device to reflow the adhesion layer, wherein the aperture is smooth and free of sharp corners.

* * * * *